United States Patent
Homma et al.

(12)

(10) Patent No.: US 6,174,727 B1
(45) Date of Patent: Jan. 16, 2001

(54) METHOD OF DETECTING MICROSCOPIC DEFECTS EXISTING ON A SILICON WAFER

(75) Inventors: Takayuki Homma, Tokyo (JP); Christopher E. D. Chidsey, San Francisco, CA (US); Masaharu Watanabe, Tokyo (JP)

(73) Assignees: Komatsu Electronic Metals, Co., Kanagawa (JP); The University Board of Trustees of the Leland Stanford Junior, Stanford, CA (US)

(*) Notice: Under 35 U.S.C. 154(b), the term of this patent shall be extended for 0 days.

(21) Appl. No.: 09/185,428

(22) Filed: Nov. 3, 1998

(51) Int. Cl.[7] .......................... G01N 31/00; G01N 19/02
(52) U.S. Cl. ................... 436/5; 73/105; 250/307; 250/311
(58) Field of Search ................... 436/5; 73/104, 73/105; 250/307, 311, 362, 341.4, 368

(56) References Cited

U.S. PATENT DOCUMENTS

| | | | | |
|---|---|---|---|---|
| 4,172,224 | * | 10/1979 | Lapinski et al. ............ | 250/302 |
| 5,242,831 | * | 9/1993 | Oki .......................... | 436/5 |
| 5,602,329 | * | 2/1997 | Haubensak ................ | 73/82 |
| 6,087,179 | * | 7/2000 | Beriozkina et al. ........ | 436/5 |
| 6,097,484 | * | 8/2000 | McIntosh et al. .......... | 356/237.5 |

* cited by examiner

*Primary Examiner*—Jill Warden
*Assistant Examiner*—Dwayne K. Handy
(74) *Attorney, Agent, or Firm*—Welsh & Katz, Ltd.

(57) ABSTRACT

A silicon wafer having microscopic defects is immersed into the diluted hydrofluoric acid with spiking metal salt such as $CuSO_4.5H_2O$ for 1 to 3 minutes. After immersing, metals which have selectively deposited on the microscopic defects are detected by using particle counters.

9 Claims, 5 Drawing Sheets

METHOD OF DETECTING MICROSCOPIC DEFECTS EXISTING ON A SILICON WAFER

BACKGROUND OF THE INVENTION

1. Field of the Invention

This invention relates to a method of detecting microscopic defects existing on a silicon wafer, and especially relates to a method of detecting microscopic defects existing on a silicon wafer which is effective to sensitively detect microscopic defects existing on a silicon wafer.

2. Description of the Prior Art

As the design rule of the integrated semiconductor devices shrinks smaller and smaller, it is required to further minimize the defects at the silicon wafer surfaces, such as pits, scratches, precipitation or deposition of organic, inorganic, and metal particles, especially the ones with sub $\mu$m scale.

In order to achieve the above requirement, consideration to the detailed characterization of these defects is desired. Currently, the "particle counters" which employ light scattering method are widely used among silicon wafer manufacturing factories and semiconductor device manufacturing factories to detect these defects.

However, the resolution limits of the "particle counters" are some 100 nm or larger and further smaller defects, which potentially cause serious degradation of the yield for the next generation devices with further smaller design scale, cannot be detected.

There are other techniques to detect these microscopic defects or deposited species, such as the one using radio isotope methods. However, these techniques require complicated preparation procedure and special expensive set-ups.

SUMMARY OF THE INVENTION

An object of this invention is to provide a method of detecting microscopic defects existing on a silicon wafer which is effective to sensitively detect microscopic defects existing on a silicon wafer.

The feature of this invention, which achieves the above object, is selectively depositing metals on microscopic defects existing on a silicon wafer. By depositing the metals on the microscopic defects, these defects are selectively decorated and can be easily detected by the conventional methods such as "particle counters".

BRIEF DESCRIPTION OF THE DRAWINGS

The various features of novelty which characterize this invention are pointed out with particularity in the claims annexed to and forming a part of this specification. For a better understanding of this invention, its operating advantages, and specific objects attained by its use, reference should be made to the accompanying drawing and descriptive matter in which there is illustrated and described a preferred embodiment of this invention.

This invention disclosed herein will be understood better with reference to the following drawings of which.

DETAILED DESCRIPTION OF THE INVENTION (The first mode)

The first mode of this invention concerns depositing metals on microscopic defects. As described above, it is difficult to detect the microscopic defects. Considering the difficulty, the inventors of this invention pay attention to overlay the microscopic defects by other substances. Generally, it can be thought that the microscopic defects existing on the silicon wafer have negative electric potential when immersed into a solution. Therefore, the substances having positive electric potential easily attached to the microscopic defects.

The first mode of this invention is constructed in view of the above aspect, and provides the technique for overlaying the microscopic defects.

Figure 1:
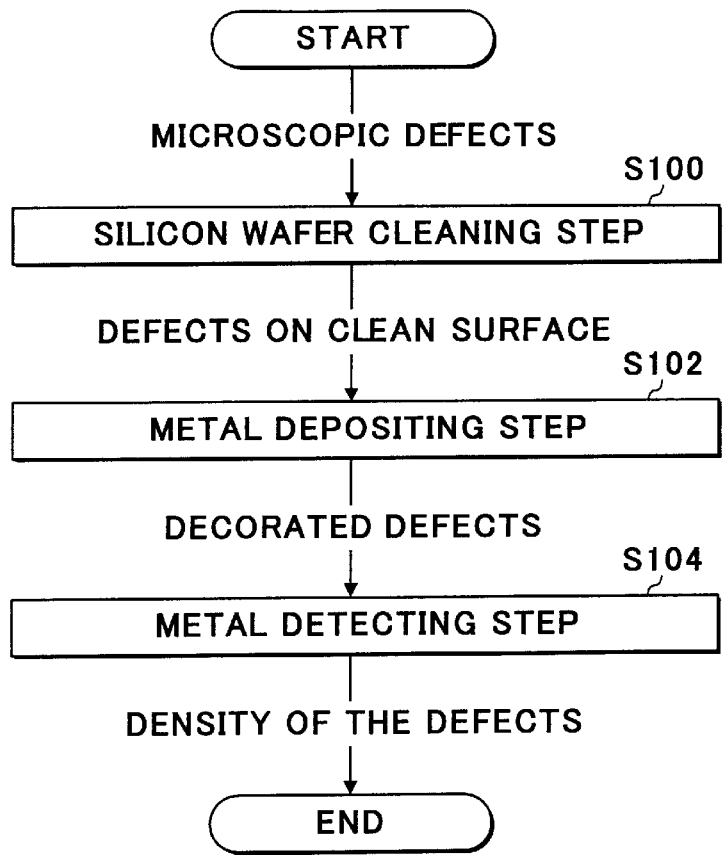
FIG. 1 is a process diagram which shows the execution procedure of the method of detecting microscopic defects existing on the silicon wafer in accordance with the first mode of this invention.

FIG. 1 is a process diagram which shows the execution procedure of the method of detecting microscopic defects existing on the silicon wafer in accordance with the first mode of this invention. Hereafter, a series of the steps shown in this figure is explained as follows:

A silicon wafer cleaning step S100 is a step in which the silicon wafer is cleaned in order to remove organic and metal contamination absorbed on the surface of the silicon wafer.

For example, this step is performed by immersing into a cleaning solvent such as hydrofluoric acid or the mixture of hydrogen peroxide and sulfuric acid.

Figure 2:
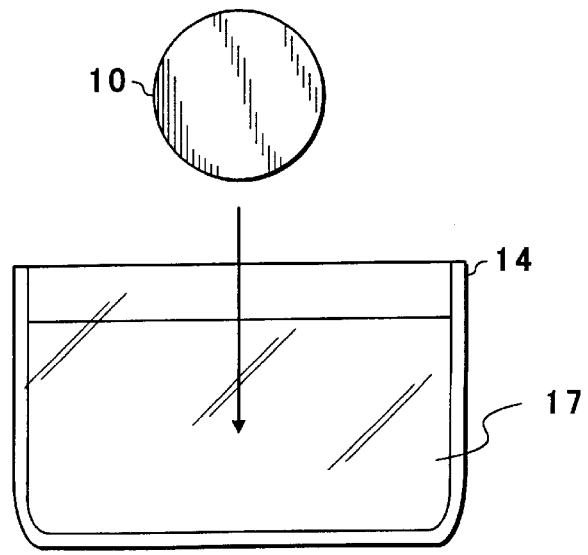
FIG. 2 is a conception diagram which shows that the silicon wafer 10 is immersed into the cleaning solvent 17.

FIG. 2 is a conception diagram which shows the state that the silicon wafer 10 is immersed into the cleaning solvent 17. As shown in this figure, in the silicon wafer cleaning step S100, the silicon wafer 10 having microscopic defects (not shown because these are microscopic) is immersed into the cleaning solvent 17 filled in the vial 14.

Figure 3:
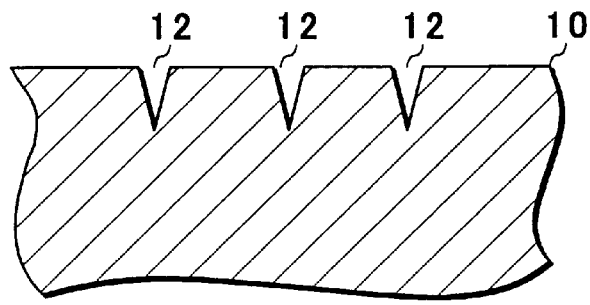
FIG. 3 is an enlarged sectional view which shows the surface of the silicon wafer 10 with the microscopic defects 12 at the surface after performing the silicon wafer cleaning step S100.

FIG. 3 is an enlarged sectional view which shows the surface of the silicon wafer 10 after performing the silicon wafer cleaning step S100. As shown in this figure, the microscopic defects 12 exist on the silicon wafer 10 in a state where the metal contamination has been removed.

A metal depositing step S102 is a step in which metals are selectively deposited on the microscopic defects. This step is performed by immersing the silicon wafer 10 into an aqueous solution containing metal ions.

Figure 4:
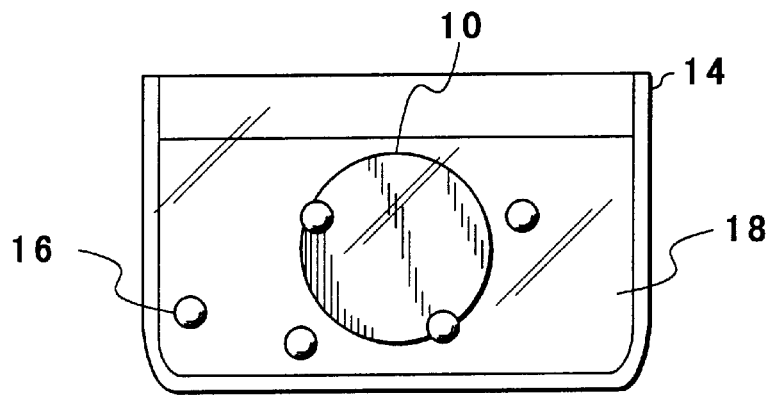
FIG. 4 is a conception diagram which shows that the silicon wafer 10 is immersed into the aqueous solution 18 containing the metal ions 16.

FIG. 4 is a conception diagram which shows the state that the silicon wafer 10 is being immersed into the aqueous solution 18 containing the metal ions 16. As shown in this figure, the metal depositing step S102 is performed in a state where the silicon wafer 10 is being immersed in the aqueous solution 18 containing metal ions 16. Preferably, the silicon wafer 10 is being immersed for 1 to 3 minutes.

The metal ions 16 are cations in the aqueous solution 18, which have positive electric potential. Consequently, these metal ions 16 are easily attached to the microscopic defects, which have negative electric potential. In terms of the ionization, the precious metals such as gold and silver, and other transition metals such as nickel, cobalt, molybdenum and iron can be used as the material of the metal ions 16. Especially, copper ions are preferable because decoration with copper was confirmed by the inventors of this invention.

A solution which hardly damages the silicon wafer 10 and easily keeps the ionization state is used as the aqueous solution 18. Preferably, diluted hydrofluoric acid is used. In the case of using the diluted hydrofluoric acid, a natural oxide film formed on the silicon wafer 10 is dissolved by the hydrofluoric acid. As a result, the bare surface is obtained.

Preferably, a concentration of the hydrofluoric acid ranges from 0.01% to 10% and a concentration of the copper ions ranges from 10 ppbw (parts per billion weight) to 100 ppmw (parts per million weight). In the case of using above concentrations, the microscopic defects are overlaid more selectively.

Figure 5:
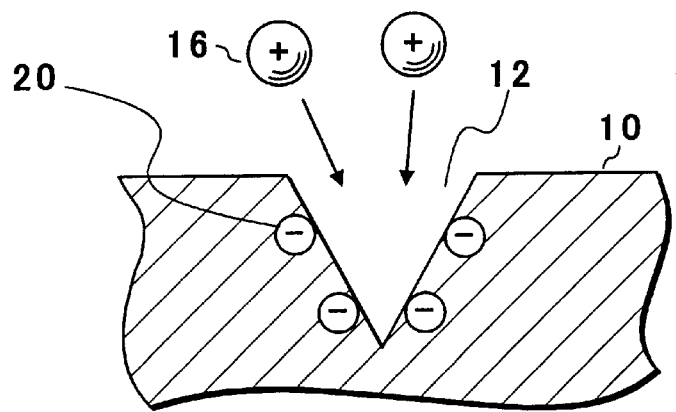
FIG. 5 is a conception diagram which shows the attracting action of the metal ions 16 in the metal depositing step S102.

FIG. 5 is a conception diagram which shows the attracting action of the metal ions 16 in the metal depositing step S102. As shown in this figure, negative charges 20 exist along the defect site of the silicon wafer 10 at which the microscopic defects 12 are formed.

Therefore, the metal ions 16 having positive electric potential are attracted the negative charge 20, and then reductive reaction of the metal ions 16 is caused.

Figure 6:
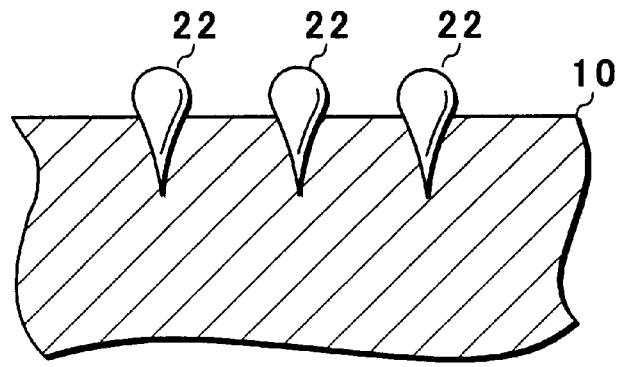
FIG. 6 is an enlarged sectional view which shows the surface of the silicon wafer 10 in a state where the microscopic defects 12 are overlaid by deposited metals 22.

FIG. 6 is an enlarged sectional view which shows the surface of the silicon wafer 10 in a state where the microscopic defects 16 are overlaid. As shown in this figure, metals 22 are deposited on the defect sites at which the microscopic defects 12 exist.

A metal detecting step S104 is a step in which the deposited metals 22 on the microscopic defects 12 in the metal depositing step S102 are detected. The deposited metals 22 can be detected by using the conventional tool such as "particle counters" because the size of the deposited metals 22 are sufficiently larger than that of the microscopic defects 12.

Furthermore, the deposited metals 22 differs in characteristics from the silicon wafer 10. For example reflectance, color and so on. Therefore, it is easy to distinguish the deposited metals 22 from the silicon wafer 10.

As explained above, according to the first mode of this invention, the detection sensitivity can be improved because The microscopic defects are overlaid by the metals.

(The second mode)

The second mode of this invention concerns selectivity control. As described above, in this invention, the microscopic defects are selectively overlaid by the metals. The selectivity of the overlaying operation is important in this invention because with high contrast between the metals and the silicon wafer, detecting operation can be easily performed.

The second mode of this invention is constructed in view of the above aspect, and provides the technique for controlling the selectivity of overlaying operation.

Figure 7:
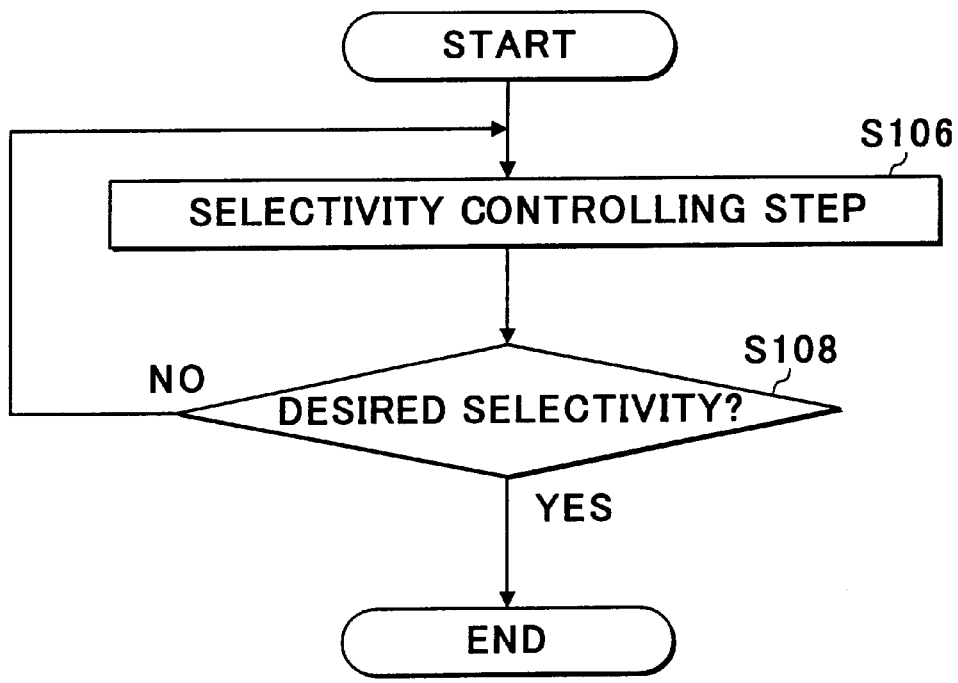
FIG. 7 is a process diagram which shows the execution procedure of the metal depositing step S102 in FIG. 1 in accordance with the second mode of this invention.

FIG. 7 is a process diagram which shows the execution procedure of the metal depositing step S102 in FIG. 1 in accordance with the second mode of this invention. The metal depositing step S102 of the second mode has a more preferable construction than that of the first mode. As shown in FIG. 7, the second mode of this invention comprises a selectivity controlling step S106, which is the feature of this second mode.

The selectivity controlling step S106 is a step in which the selectivity with which the metals 22 are deposited on the microscopic defects 12. As described above, metal deposition proceeds according to the reductive reaction of the metal ions 16. Therefore, controlling the rate of reductive reaction of the metal ions 16 varies the electivity of depositing the metals 22.

The first approach for controlling the selectivity is adjusting an electric potential of the silicon wafer 10. For example, negative bias voltage is applied to the silicon wafer 10, and then the negative charges 20 increase along the defect site of the silicon wafer 10 at which the microscopic defects 12 are formed. As a result of which, the metal ions 16 are more strongly attracted to the microscopic defects 12.

However, if the negative bias voltage is too strong, the negative charges 20 distribute along the surface of the silicon wafer 10. Therefore, appropriate voltage is applied to the silicon wafer 10.

The second approach for controlling the selectivity is adjusting a temperature of the aqueous solution 18. The rate of the reductive reaction of the metal ions 16 changes when the temperature of the aqueous solution 18 changes. Therefore, the selectivity can be controlled by adjusting the temperature of the aqueous solution 18.

The third approach for controlling the selectivity is adjusting a light illumination irradiating the silicon wafer in the aqueous solution 18.

As well as the case of adjusting the temperature, the rate of the reductive reaction of the metal ions 16 changes when the light illumination irradiating the silicon wafer 10 in the aqueous solution 18 changes. Therefore, the selectivity can be controlled by adjusting the light illumination irradiating the silicon wafer 10 in the aqueous solution 18.

The fourth approach for controlling the selectivity is adding one or more than two chelating agents into the aqueous solution 18. It is known that the metal ion 16 forms complex with chelating agents in aqueous solution, which shifts the potential of the electrochemical reduction of the metal ions 16. Therefore, the selectivity can be controlled by adjusting the variation and concentration of the chelating agents into the aqueous solution 18.

As shown in FIG. 7, the selectivity controlling step S106 is repeated until the desired selectivity is achieved (step S108).

As explained above, according to the second mode of this invention, the contrast between the metals 22 and the silicon wafer 10 can be improved because the selectivity of the overlaying operation is appropriately controlled.

DESCRIPTION OF THE PREFERRED EMBODIMENT

The preferred embodiment of this invention is performed in a series of the following steps.

STEP 1. Preparation of Test Samples

P-type silicon (100) wafers were used. In order to confirm the selective deposition condition of metals at the surface defect sites, three kinds of the wafers, A, B, and C with different surface defect densities were prepared. The surface of the wafer A is in the as-prepared condition, while the wafers B and C are either re-polished using a chemical-mechanical planarization (CMP) process or treated on the front side with what is normally a "back-side" damaging (hereinafter referred to as "BSD") process using a jet of water containing fine particles of $SiO_2$ respectively.

STEP 2. Pre-treatment of the Test Samples

The wafers A, B and C were immersed in 4 volume of 96% $H_2SO_4$ to 1 volume of 30% aqueous $H_2O_2$ for 10 min at 120° C., followed by rinsing with ultra-pure water. Then the wafers were immersed into an aqueous solution of 2.0 volume % dilute hydrofluoric acid (DHF) for 1 minute. As a result of which, the wafers A, B and C had been cleaned.

STEP 3. Surface Topographies of the Test Samples

Scanning tunneling microscopy (STM) observation of the wafers A, B and C over 5 μm×5 μm area was conducted after the pre-treatment.

Figure 8:
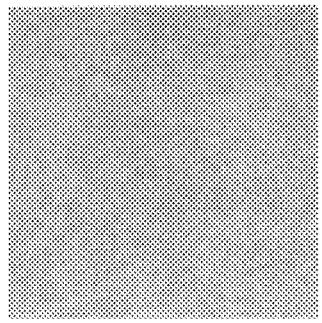
FIG. 8 is a STM image which shows the surface of the wafer A over 5 $\mu$m×5 $\mu$m area.

FIG. 8 is a STM image which shows the surface of the wafer A over 5 μm×5 μm area.

Figure 9:
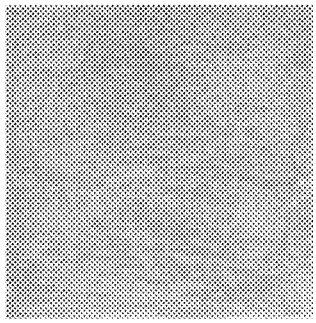
FIG. 9 is a STM image which shows the surface of the wafer B over 5 $\mu$m×5 $\mu$m area.

FIG. 9 is a STM image which shows the surface of the wafer B over 5 μm×5 μm area.

Figure 10:
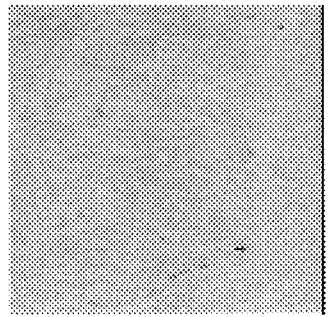
FIG. 10 is a STM image which shows the surface of the wafer C over 5 $\mu$m×5 $\mu$m area.

FIG. 10 is a STM image which shows the surface of the wafer C over 5 μm×5 μm area.

As shown in the FIGS. 8 and 9, it is found that the wafers A and B have almost defect-free surface.

On the other hand, several defects with pit-like and scratch-like structures with some 100 nm size are observed in the case of the wafer C, as is shown in FIG. 10. From the image in FIG. 10, the density of the defects at the surface of the wafer C is estimated to be several to ten defects/$(5 \mu m)^2$.

Figure 11:
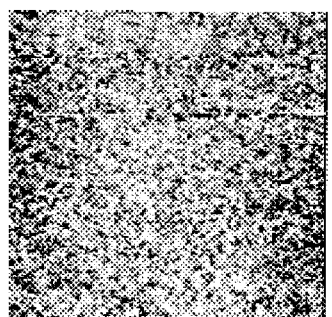
FIG. 11 is a STM image which shows the surface of the wafer A with higher magnification (500 nm×500 nm).

FIG. 11 is a STM image which shows the surface of the wafer A with higher magnification (500 nm×500 nm).

Figure 12:
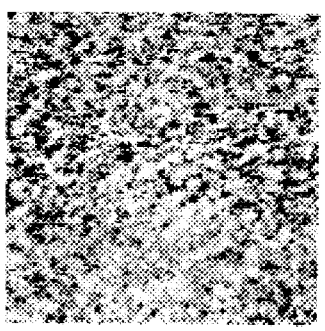
FIG. 12 is a STM image which shows the surface of the wafer B with higher magnification (500 nm×500 nm).

FIG. 12 is a STM image which shows the surface of the wafer B with higher magnification (500 nm×500 nm).

Figure 13:
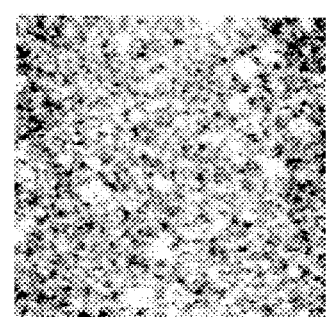
FIG. 13 is a STM image which shows the surface of the wafer C with higher magnification (500 nm×500 nm).

FIG. 13 is a STM image which shows the surface of the wafer C with higher magnification (500 nm×500 nm).

As is expected, the wafers with (100) surface possess atomically rough features consisting of micro-facets. As shown in FIG. 11, little damages are introduced on the wafer A. On the other hand, the damages introduced on the wafer B are greater than those of the wafer A as shown in FIG. 12. The damages of the wafer B are caused by the re-polishing. And as shown in FIG. 13, there are great damages on the wafer C. The damages of the wafer C are caused by the BSD treatment, and are greater than those of the wafer B.

STEP 4. Metal Overlaying of the Test Samples

Immediately after the pre-treatment (step 2) described above, the wafers A, B and C were immersed into the DHF in separate vials with spiking metal salt such as $CuSO_4.5H_2O$ for prescribed period.

The overlaying of defect sites by deposition of trace amount of metals in the solution is examined. By varying the deposition parameters such as concentration of the metal salts and the immersion time, the deposition condition of the surface has been changed.

EXAMPLE 1

The wafers A and C were immersed into 200 μM of $CuSO_4$ spiked DHF for 3 minutes after the pre-treatment (step 2).

After immersing, scanning tunneling microscopy (STM) observation of the wafers A and C over 5 μm×5 μm area was conducted.

Figure 14:
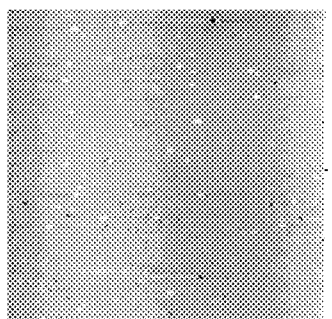
FIG. 14 is a STM image which shows the surface of the wafer A over 5 $\mu$m×5 $\mu$m area after immersing for 3 minutes.

FIG. 14 is a STM image which shows the surface of the wafer A over 5 μm×5 μm area after immersing for 3 minutes.

Figure 15:
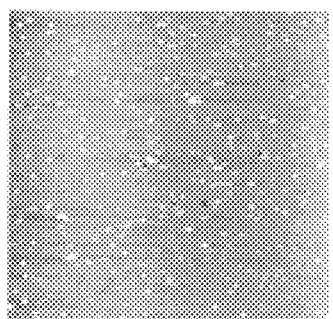
FIG. 15 is a STM image which shows the surface of the wafer C over 5 $\mu$m×5 $\mu$m area after immersing for 3 minutes.

FIG. 15 is a STM image which shows the surface of the wafer C over 5 μm×5 μm area after immersing for 3 minutes.

As is seen in the FIGS. 14 and 15, numerous formation of deposits occurs at the surface of both wafers, and the wafer C possesses higher density of the deposits. The size of the deposits is several tens of nanometers diameter for both wafers, however, some larger deposits with 100–200 nm diameter can be seen on the wafer C.

As is described above, the wafer A has the defect free surface whereas the wafer C has the defects with 100–200 nm scale with the density of several to ten defects/$(5 \mu m)^2$, which seems to correspond to the density of the "larger" deposits in FIG. 15.

The wafers A and C were immersed into 200 μM of $CuSO_4$ spiked DHF for 3 minutes after the pre-treatment (step 2).

EXAMPLE 2

The wafers A, B and C were immersed into 200 μM of $CuSO_4$ spiked DHF for 1 minute after the pre-treatment (step 2).

After immersing, scanning tunneling microscopy (STM) observation of the wafers A, B and C over 5 μm×5 μm area was conducted.

Figure 16:
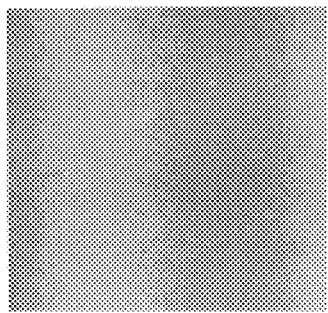
FIG. 16 is a STM image which shows the surface of the wafer A over 5 $\mu$m×5 $\mu$m area after immersing for 1 minute.

FIG. 16 is a STM image which shows the surface of the wafer A over 5 μm×5 μm area after immersing for 1 minute.

Figure 17:
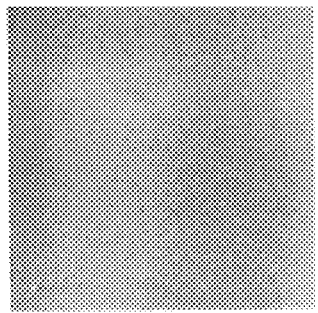
FIG. 17 is a STM image which shows the surface of the wafer B over 5 $\mu$m×5 $\mu$m area after immersing for 1 minute.

FIG. 17 is a STM image which shows the surface of the wafer B over 5 μm×5 μm area after immersing for 1 minute.

Figure 18:
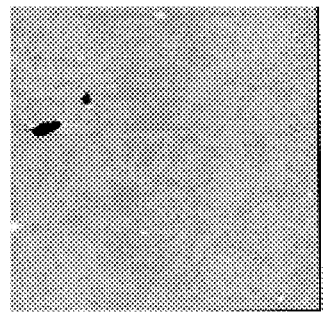
FIG. 18 is a STM image which shows the surface of the wafer C over 5 $\mu$m×5 $\mu$m area after immersing for 1 minute.

FIG. 18 is a STM image which shows the surface of the wafer C over 5 μm×5 μm area after immersing for 1 minute.

In these images, no apparent deposits can be seen on the wafers A and B. On the other hand, several deposits can be observed around the defect sites of the wafer C.

Figure 19:
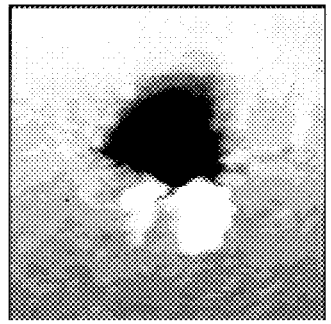
FIG. 19 is a representative close-up image of the FIG. 17 which shows the pit-like defect site of the wafer C over 400 nm×400 nm area.

FIG. 19 is a representative close-up image of the FIG. 17 which shows the pit-site of the wafer C over 400 nm×400 nm area. As shown in this figure, the deposition occurs at the edge portion of the pit-site.

Figure 20:
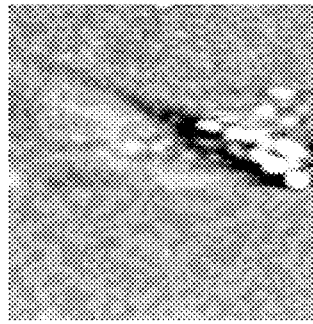
FIG. 20 is a representative close-up image of the FIG. 17 which shows the scratch-like defect site of the wafer C over 400 nm×400 nm area.

FIG. 20 is a representative close-up image of the FIG. 17 which shows the scratch-site of the wafer C over 400 nm×400 nm area. As shown in this figure, the deposition occurs at the inside portion of the scratch-site.

In both cases, the aggregates of the deposited metal atoms with several tens of nanometer diameter can be seen, indicating that the deposits with 100–200 nm size described above were formed due to the deposition of the metal atoms.

On the other hand, no apparent nucleation could be detected in the surface area except these defect-associated sites. These results strongly indicate that the defect sites possess high "deposition activity" for the trace metals, compared with a flat, non-defect area. Furthermore, the deposits at the defect sites are sufficiently large to be easily detected by the "particle counters" so that mapping of these overlaid sites can be carried out.

This invention may be embodied in other specific forms without departing from the spirit or essential characteristics thereof. The present embodiment is therefore to be considered in all respects as illustrative and not restrictive, the scope of this invention being indicated by the appended claims rather than by the foregoing description and all changes which come within the meaning and range of equivalency of the claims are therefore intended to be embraced therein.

What is claimed is:

1. A method of detecting microscopic defects existing on a silicon wafer comprising:
    a first silicon wafer cleaning step of cleaning the silicon wafer into a cleaning solvent; followed by:
        a metal depositing step of selectively depositing metals composed of the metal ions on any microscopic defects existing on the silicon wafer; and
        a metal detecting step of detecting the metals deposited on the microscopic defects in the metal depositing step, thereby detecting the microscopic defects.

2. A method of detecting microscopic defects existing on a silicon wafer as claimed in claim 1, wherein the metals are selectively deposited by a diluted hydrofluoric acid; and the metal ions are copper ions.

3. A method of detecting microscopic defects existing on a silicon wafer as claimed in claim 2, wherein a concentration of the hydrofluoric acid ranges from 0.01% to 10% by weight and a concentration of the copper ions ranges from 10 ppbw to 100 ppmw.

4. A method of detecting microscopic defects existing on a silicon wafer as claimed in claim 1, wherein the metal depositing step immerses the silicon wafer into an aqueous solution for 1 to 3 minutes.

5. A method of detecting microscopic defects existing on a silicon wafer as claimed in claim 1, wherein the metal depositing step comprises a selectivity controlling step of controlling a selectivity with which the metals are deposited on the microscopic defects.

6. A method of detecting microscopic defects existing on a silicon wafer as claimed in claim 5, wherein the selectivity controlling step controls the selectivity by adjusting an electric potential of the silicon wafer.

7. A method of detecting microscopic defects existing on a silicon wafer as claimed in claim 5, wherein the selectivity controlling step controls the selectivity by adjusting the temperature of an aqueous solution.

8. A method of detecting microscopic defects existing on a silicon wafer as claimed in claim 5, wherein the selectivity controlling step controls the selectivity by adjusting a light illumination irradiating the silicon wafer in an aqueous solution.

9. A method of detecting microscopic defects existing on a silicon wafer as claimed in claim 5, wherein the selectivity controlling step controls the selectivity by adding one or more than two chelating agents into an aqueous solution.

* * * * *